US012776516B2

(12) United States Patent
Torres et al.

(10) Patent No.: US 12,776,516 B2
(45) Date of Patent: Oct. 27, 2026

(54) FUNCTIONALIZED CROWN ETHERS FOR LITHIUM-ION BATTERIES

(71) Applicant: SIONIC ENERGY, INC., Rochester, NY (US)

(72) Inventors: Gabriel Torres, Rochester, NY (US); John Sinicropi, Rochester, NY (US); Surya S. Moganty, Henrietta, NY (US); Dai In Park, Daejeon City (KR)

(73) Assignee: SIONIC ENERGY, INC., Rochester, NY (US)

( * ) Notice: Subject to any disclaimer, the term of this patent is extended or adjusted under 35 U.S.C. 154(b) by 585 days.

(21) Appl. No.: 18/358,469

(22) Filed: Jul. 25, 2023

(65) Prior Publication Data

US 2024/0039047 A1 Feb. 1, 2024

Related U.S. Application Data

(60) Provisional application No. 63/392,025, filed on Jul. 25, 2022.

(51) Int. Cl.

| | |
|---|---|
| ***H01M 10/0567*** | (2010.01) |
| ***C07D 327/00*** | (2006.01) |
| ***C07F 9/6571*** | (2006.01) |
| ***H01M 10/0568*** | (2010.01) |
| ***H01M 10/0569*** | (2010.01) |

(52) U.S. Cl.

CPC ...... *H01M 10/0567* (2013.01); *C07D 327/00* (2013.01); *C07F 9/657118* (2013.01); *H01M 10/0568* (2013.01); *H01M 10/0569* (2013.01); *H01M 2300/0037* (2013.01)

(58) Field of Classification Search

CPC ......... H01M 10/0567; H01M 10/0568; H01M 10/0569; H01M 2300/0037; C07D 327/00; C07F 9/657118

See application file for complete search history.

(56) References Cited

U.S. PATENT DOCUMENTS

| | | | | |
|---|---|---|---|---|
| 2021/0167422 | A1* | 6/2021 | Omichi | H01M 10/05 |
| 2021/0249714 | A1 | 8/2021 | Hayashi et al. | |
| 2021/0376382 | A1 | 12/2021 | Moganty | |

FOREIGN PATENT DOCUMENTS

| | | | |
|---|---|---|---|
| CN | 111293356 | A | 6/2020 |
| EP | 3540824 | A1 | 9/2019 |
| KR | 10-2012-0093262 | A | 8/2012 |
| KR | 10-2020-0060063 | A | 5/2020 |
| WO | 2018174574 | A1 | 9/2018 |
| WO | 2022/046174 | A1 | 3/2022 |

OTHER PUBLICATIONS

Korean Patent Application No. 10-2025-7005695 Office Action dated Jun. 10, 2025 with partial English translation, 12 pages.

European Patent Application No. 23847501.6 Search Report dated Jan. 27, 2026, 6 pages.

PubChem CID, "Methylphosphonic acid oxybisethylene ester", Japan Chemical Substance Dictionary (Nikkaji), Published Jan. 2, 2016.

International Search Report and Written Opinion from PCT Application No. PCT/US2023/070924, dated Jul. 25, 2023 transmitted by the ISA/US—Aurthorized officer Taina Matos.

* cited by examiner

*Primary Examiner* — Kimberly Wyluda

(74) *Attorney, Agent, or Firm* — Cozen O'Connor

(57) ABSTRACT

An electrolyte containing functionalized crown ethers suitable for use in electrochemical energy storage devices useful for reducing battery resistance, increasing cycle life, and improving high-temperature performance is disclosed.

27 Claims, 4 Drawing Sheets

FUNCTIONALIZED CROWN ETHERS FOR LITHIUM-ION BATTERIES

CROSS REFERENCE

This application claims the benefit of the filing date of U.S. Provisional Patent Application No. 63/392,025, filed Jul. 25, 2022, which is hereby incorporated by reference in its entirety.

FIELD

The present disclosure relates to functionalized crown ethers that are useful for reducing battery resistance, increasing cycle life, improving high-temperature performance; electrolytes containing the functionalized crown ethers; and electrochemical energy storage devices utilizing the electrolytes.

BACKGROUND

Li-ion batteries are heavily used in consumer electronics, electric vehicles (EVs), as well as energy storage systems (ESS) and smart grids. Recently, Li-ion batteries with voltages above 4.35 V have gained importance because of higher capacity and subsequent energy density benefits. However, the stability of the cathode materials at these potentials reduces due to increased oxidation. This may result in electrochemical oxidation of the material to produce gases, and that can deteriorate the performance of the battery. The cathode active material, which is capable of intercalating/deintercalating lithium ions may dissolve in the non-aqueous electrolyte, resulting in a structural breakdown of the material, and will lead to an increase in the interfacial resistance. These Li-ion batteries are also typically exposed to extreme temperatures during their operation. The SEI (Solid Electrolyte Interface) layer formed on the anode is gradually broken down at high temperatures, and hence leads to more irreversible reaction resulting in capacity loss. Similarly, the CEI (Cathode Electrolyte Interface) will also lose stability at elevated temperatures. These reactions happen on the positive and negative electrode during cycling but are generally more severe at higher temperatures due to faster kinetics. The next generation Li-ion batteries used in consumer electronics, EVs, and ESS will require significant improvements in the electrolyte component relative to the current state-of-the art of Li-ion batteries.

The shuttling of positive and negative ions between the battery electrodes is the main function of the electrolyte. Historically, researchers have focused on developing battery electrodes, and electrolyte development has been limited. Traditional Li-ion batteries used carbonate-based electrolytes with a large electrochemical window, that can transport lithium ions. These electrolytes need functional additives to passivate the anode and form a stable SEI, as well as additives for stabilizing the cathode. At the same time, there is a need to design and develop additives that allow stable and safe cycling of high voltage, high energy Li-ion batteries.

As the industry moves towards higher energy cathode materials for higher energy batteries, stable, efficient, and safe cycling of batteries in wide voltage windows is necessary. Li-ion battery electrolytes can be tuned based on their applications by addition of different co-solvents and additives. This tunability has enabled the development of different additives for high voltage stability and safety of Li-ion cells.

There have been reports in the literature of crown ethers as additives that can coordinate with metal ions, which can have a wide range of beneficial effects ranging from improving lithium solvation, decreasing charge transfer resistance, to scavenging dissolved manganese ions from the cathode (Ochida, M.; Doi, T.; Domi, Y.; Tsubouchi, S.; Nakagawa, H.; Yamanaka, T.; Abe, T.; Ogumi, Z. J. Electrochem. Soc. 2013, 160, A410, Xu, K. Chem. Rev. 2004, 104, 4303). Japanese patent JP2000195548A has reported the use crown ethers and aza-crown ethers as a component of an electrolyte for lithium secondary batteries. U.S. Pat. No. 9,130,231 reports the use of crown ethers as a component in the microporous separator of a lithium-ion battery. Chinese patent CN103613576 reports the synthesis of macrocyclic cyclic sulfates.

Herein, functionalized crown ethers are reported as additives for Li-ion batteries. These molecules when added to electrolytes allow for stabilization of the cathode and the holistic electrolyte system. The cell with this additive in the electrolyte would enable safe, long cycle life, and high energy lithium-ion batteries. Hence, there is a need to incorporate these novel additives to improve the performance of lithium-ion batteries.

SUMMARY

In accordance with one aspect of the present disclosure, there is provided a new class of compounds, and an electrolyte for an electrochemical energy storage device. The electrolyte includes: a functionalized crown ether; an aprotic organic solvent; and a metal salt.

In accordance with another aspect of the present disclosure, there is provided an electrolyte for an electrochemical energy storage device, the electrolyte includes: a functionalized crown ether; an aprotic organic solvent; a metal salt; and at least one additive.

In accordance with another aspect of the present disclosure, there is provided an electrochemical energy storage device, including: a cathode; an anode; a separator and an electrolyte including a functionalized crown ether, an aprotic organic solvent, and a metal salt.

In accordance with another aspect of the present disclosure, there is provided an electrolyte for an electrochemical energy storage device, the electrolyte includes: a functionalized crown ether; an aprotic organic solvent; a metal salt; and at least one additive; wherein the aprotic organic solvent includes open-chain or cyclic carbonate, carboxylic acid ester, nitrite, ether, sulfone, sulfoxide, ketone, lactone, dioxolane, glyme, crown ether, siloxane, phosphoric acid ester, phosphite, mono- or polyphosphazene or mixtures thereof.

In accordance with another aspect of the present disclosure, there is provided an electrolyte for an electrochemical energy storage device, the electrolyte includes: a functionalized crown ether; an aprotic organic solvent; a metal salt; and at least one additive; wherein the cation of the metal salt is aluminum, magnesium or an alkali metal, such as lithium or sodium.

In accordance with another aspect of the present disclosure, there is provided an electrolyte for an electrochemical energy storage device, the electrolyte includes: a functionalized crown ether; an aprotic organic solvent; a metal salt; and at least one additive; wherein the additive contains a compound containing at least one unsaturated carbon-carbon bond, carboxylic acid anhydride, sulfur-containing compound, phosphorus-containing compounds boron-containing compound, silicon-containing compound or mixtures thereof.

These and other aspects of the present disclosure will become apparent upon a review of the following detailed description and the claims appended thereto.

DETAILED DESCRIPTION

Figure 1:
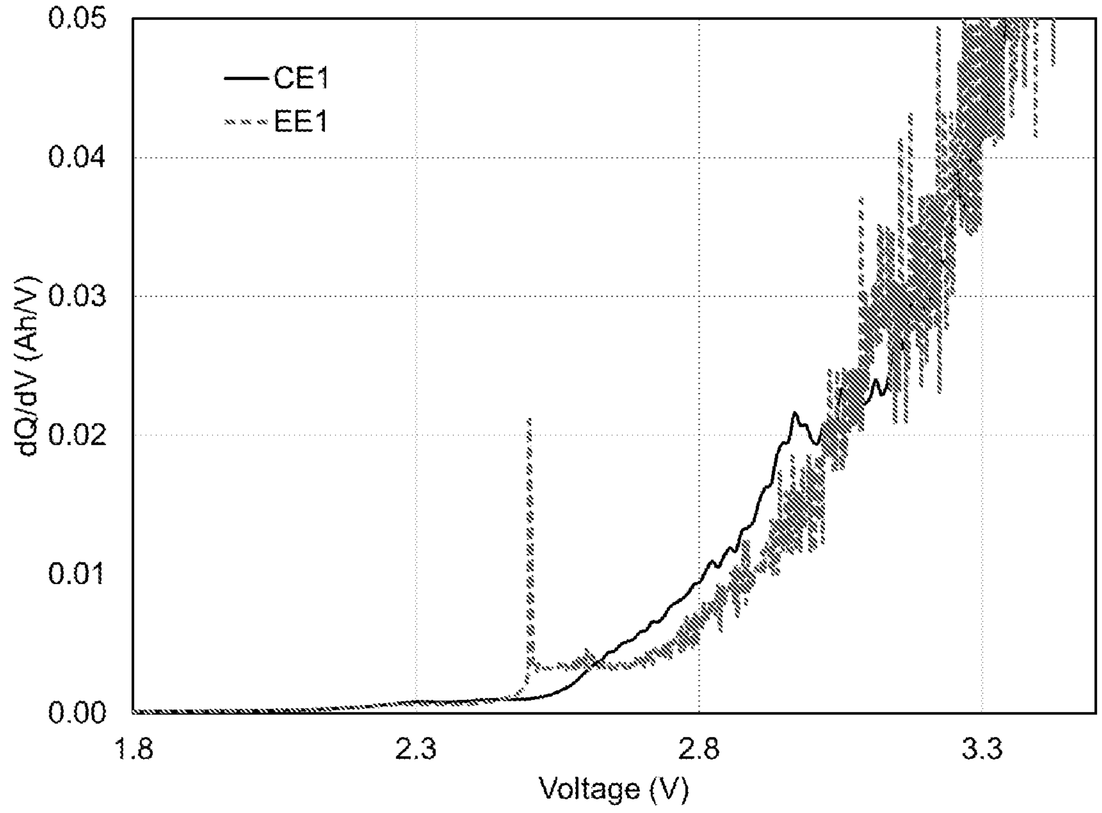
FIG. 1 shows a differential capacity profile of cell formation for the dQ/dV profiles of electrolytes tested in NMC622/Gr cells.

The disclosed technology relates generally to lithium-ion (Li-ion) battery electrolytes. Particularly, the disclosure is directed towards a functionalized crown ether including either at least one oxygen-phosphorus bond or at least one oxygen-sulfur bond; electrolytes containing these functionalized crown ether materials; and electrochemical energy storage devices containing these electrolytes.

The present disclosure describes a Li-ion battery electrolyte with an electrolyte formulation that can overcome cathode stability challenges in Li-ion batteries, particularly those including cathode materials with a high nickel content at high voltage. Current state-of-the-art Li-ion batteries include cathode materials that are low in nickel content and operate at high voltage or have high nickel content but operate at a low voltage. State-of-the-art electrolytes are tuned towards these conditions, and researchers have recently started focusing on enabling high nickel, high voltage battery cathodes with novel electrolyte formulations. There is a need to develop an electrolyte solution for cycling of Li-ion cells with high voltage, high nickel cathodes. The present technology is based on an innovative functionalized crown ether, that when incorporated in the electrolyte can improve the stability of high-voltage, high-energy cathodes. The electrolyte ethers form a unique cathode electrolyte interface (CEI) and do not excessively passivate the cathode, when used at low weight loadings. Additionally, an improved CEI improves the high temperature performance and storage stability, with no effect at room temperature.

In an embodiment, an electrochemical energy storage device electrolyte includes a) an aprotic organic solvent; b) a metal salt; c) a functionalized crown ether compound material. In an embodiment, the functionalized crown ether compound material is present in a concentration from 0.01 wt. % to 10 wt. % of the electrolyte.

In an aspect of the disclosure, the molecular structure of at least one functionalized crown ether organic compound according to the formulas I, II, or III

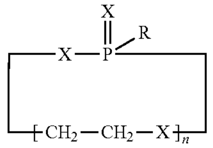

(I)

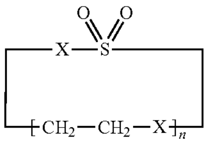

(II)

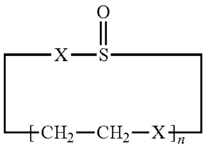

(III)

wherein:

n is an integer ranging from 1 to 8;

X is independently oxygen or sulfur; and

R is independently a halogen, oxygen or sulfur atom further bonded to $C_1$-$C_{12}$ substituted or unsubstituted alkyl groups, or $C_6$-$C_{14}$ aryl group, wherein any hydrogen atom can be replaced with or carbon atom can be unsubstituted or can be substituted with an epoxide, halogen, alkyl, alkoxy, perfluorinated alkyl, silyl, siloxy, silane, sulfoxide, amide, azo, ether, and thioether group or combination thereof.

Specific examples of molecules according to the disclosure are listed below:

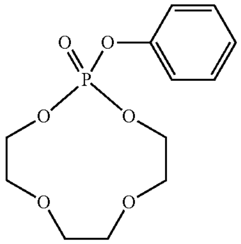

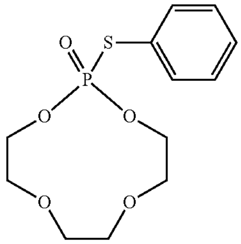

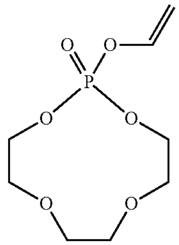

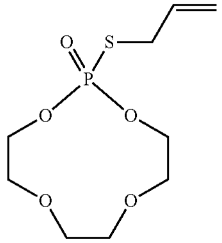

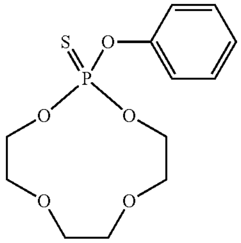

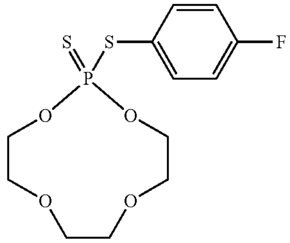

-continued
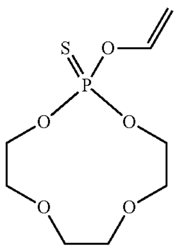
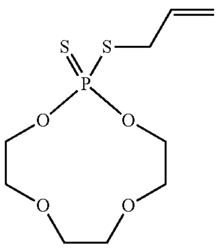
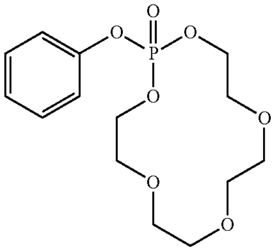
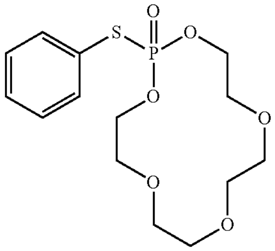
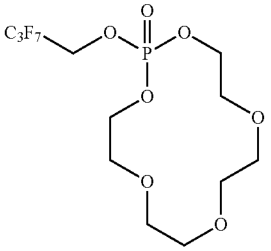
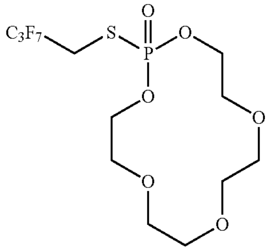
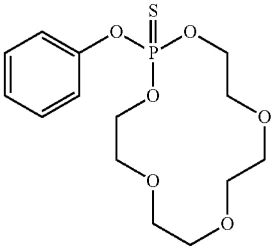
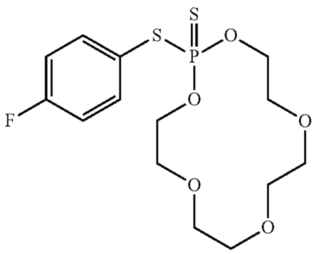
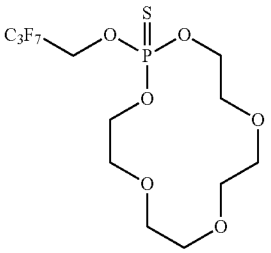
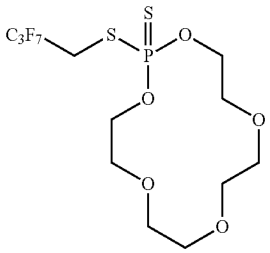
-continued
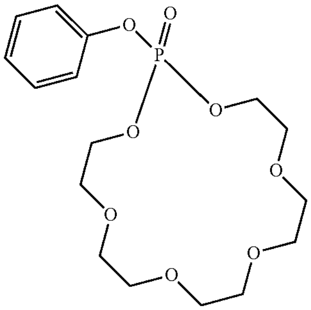
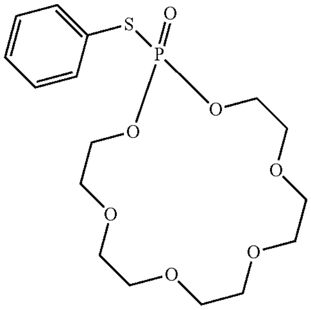
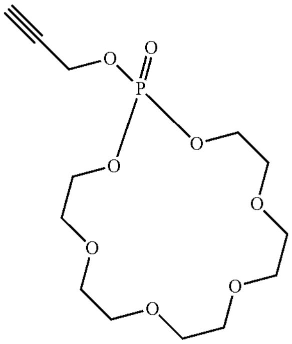
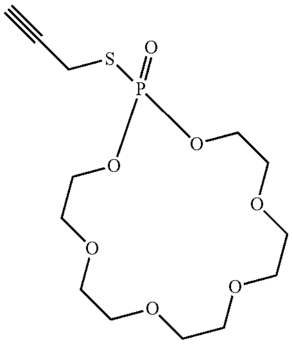
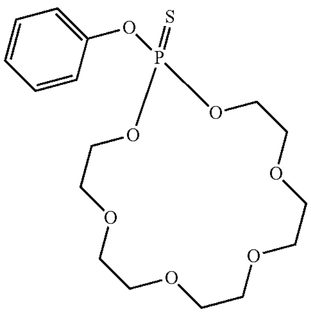

-continued

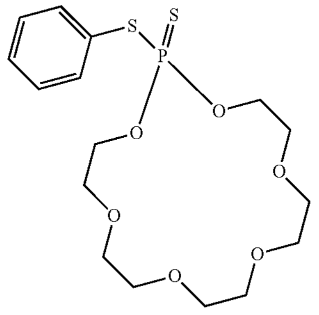

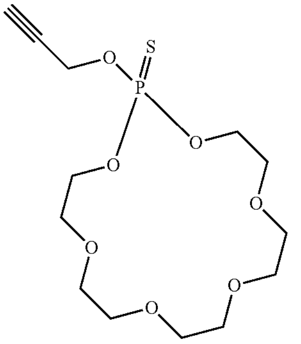

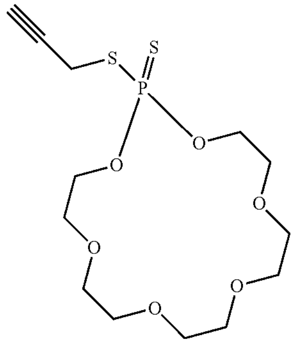

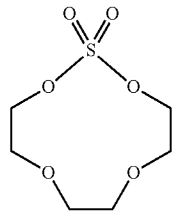

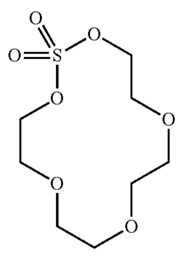

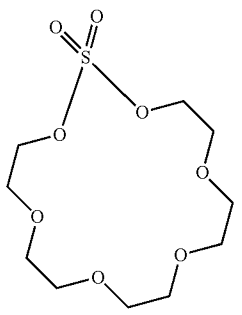

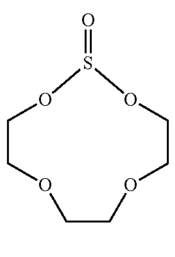

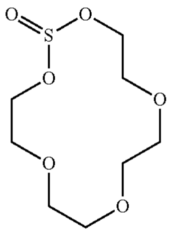

-continued

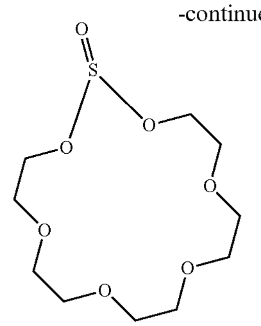

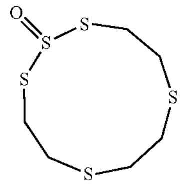

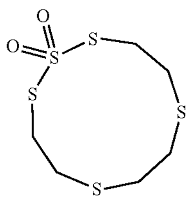

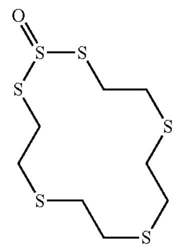

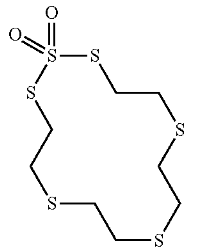

These examples are only an illustration and are not meant to limit the disclosure of claims to follow.

The addition of a functionalized crown ether into the Li-ion battery system allows for the sequestration of metal ions and stabilization of the surface of the cathode. The resulting effect suppresses further oxidative decomposition of the rest of the electrolyte components that occurs otherwise in contact with the cathode material. The inclusion of a phosphorus-oxygen bond can ensure good coordination with high nickel, high energy cathode materials.

The disclosure also includes a method for synthesizing a functionalized crown ether, and the use of such molecules in lithium-ion battery electrolytes. These molecules impart greater stability to the electrolytes and cathodes operating at higher potentials.

In an aspect of the disclosure, the electrolyte includes a metal salt. In an embodiment, the metal salt is present in the electrolyte in a range of from 10% to 30% by weight. In an embodiment, the cation of the metal salt is aluminum, magnesium or an alkali metal, such as lithium or sodium. A variety of lithium salts may be used, including, for example, $Li(AsF_6)$; $Li(PF_6)$; $Li(CF_3CO_2)$; $Li(C_2F_5CO_2)$; $Li(CF_3SO_3)$; $Li[N(CP_3SO_2)_2]$; $Li[C(CF_3SO_2)_3]$; $Li[N(SO_2C_2F_5)_2]$; $Li(ClO_4)$; $Li(BF_4)$; $Li(PO_2F_2)$; $Li[PF_2(C_2O_4)_2]$; $Li[PF_4C_2O_4]$; lithium alkyl fluorophosphates; $Li[B(C_2O_4)_2]$; $Li[BF_2C_2O_4]$; $Li_2[B_{12}Z_{12-j}H_j]$; $Li_2[B_{10}X_{10-j'}H_{j'}]$; or a mixture of any two or more thereof, wherein Z is independent at each occurrence a halogen, j is an integer from 0 to 12 and j' is an integer from 1 to 10.

In an aspect of the disclosure, the electrolyte includes an aprotic organic solvent selected from open-chain or cyclic carbonate, carboxylic acid ester, nitrite, ether, sulfone, sulfoxide, ketone, lactone, dioxolane, glyme, crown ether, siloxane, phosphoric acid ester, phosphite, mono- or polyphosphazene or mixtures thereof. In an embodiment, the solvent is present in the electrolyte in a range of from 50% to 90% by weight.

Examples of aprotic solvents for generating electrolytes include but are not limited to dimethyl carbonate, ethyl methyl carbonate, diethyl carbonate, methyl propyl carbonate, ethyl propyl carbonate, dipropyl carbonate, propylene carbonate, ethylene carbonate, fluoroethylene carbonate, bis(trifluoroethyl) carbonate, bis(pentafluoropropyl) carbonate, trifluoroethyl methyl carbonate, pentafluoroethyl methyl carbonate, heptafluoropropyl methyl carbonate, perfluorobutyl methyl carbonate, trifluoroethyl ethyl carbonate, pentafluoroethyl ethyl carbonate, heptafluoropropyl ethyl carbonate, perfluorobutyl ethyl carbonate, etc., fluorinated oligomers, methyl propionate, ethyl propionate, butyl propionate, dimethoxyethane, triglyme, tetraethyleneglycol, dimethyl ether, polyethylene glycols, triphenyl phosphate, tributyl phosphate, hexafluorocyclotriphosphazene, 2-Ethoxy-2,4,4,6,6-pentafluoro-1,3,5,2-5,4-5,6-5 triazatriphosphinine, triphenyl phosphite, sulfolane, dimethyl sulfoxide, ethyl methyl sulfone, ethylvinyl sulfone, allyl methyl sulfone, divinyl sulfone, fluorophenylmethyl sulfone and gamma-butyrolactone.

In an aspect of the disclosure, the electrolytes further include at least one additive to protect the electrodes and electrolyte from degradation. Thus, electrolytes of the present technology may include an additive that is reduced or polymerized on the surface of an electrode to form a passivation film on the surface of an electrode.

In an embodiment, an additive is a substituted or unsubstituted linear, branched, or cyclic hydrocarbon including at least one oxygen atom and at least one aryl, alkenyl or alkynyl group. The passivating film formed from such additives may also be formed from a substituted aryl compound or a substituted or unsubstituted heteroaryl compound where the additive includes at least one oxygen atom.

Representative additives include glyoxal bis(diallyl acetal), tetra(ethylene glycol) divinyl ether, 1,3,5-triallyl-1,3,5-triazine-2,4,6(1H,3H,5H)-trione, 1,3,5,7-tetravinyl-1,3,5,7-tetramethylcyclotetrasiloxane, 2,4,6-triallyloxy-1,3,5-triazine, 1,3,5-triacryloylhexahydro-1,3,5-triazine, 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2-amino-3-vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2-vinyloxetane, 2-vinyloxy-cyclopropanone, 3-(N-vinylamino)cyclohexanone, 3,5-divinyl furoate, 3-vinylazetidin-2-one, 3 vinylaziridin-2-one, 3-vinylcyclobutanone, 3-vinylcyclopentanone, 3-vinyloxaziridine, 3-vinyloxetane, 3-vinylpyrrolidin-2-one, 2-vinyl-1,3-dioxolane, acrolein diethyl acetal, acrolein dimethyl acetal, 4,4-divinyl-3-dioxolan-2-one, 4-vinyltetrahydropyran, 5-vinylpiperidin-3-one, allylglycidyl ether, butadiene monoxide, butyl-vinyl-ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, β-vinyl-γ-butyrolactone or a mixture of any two or more thereof. In some embodiments, the additive may be a cyclotriphosphazene that is substituted with F, alkyloxy, alkenyloxy, aryloxy, methoxy, allyloxy groups, sulfonic acid groups, or combinations thereof. For example, the additive may be a (divinyl)-(methoxy)(trifluoro)cyclotriphosphazene, (trivinyl)(difluoro)(methoxy) cyclotriphosphazene, (vinyl)(methoxy)(tetrafluoro)cyclotriphosphazene, (aryloxy)(tetrafluoro)(methoxy) cyclotriphosphazene, (methyl sulfonyl) cyclotriphosphazene, or (diaryloxy)(trifluoro)(methoxy) cyclotriphosphazene compounds or a mixture of two or more such compounds.

In some embodiments the additive is a sulfur-containing compound, phosphorus-containing compound, boron-containing compound, silicon-containing compound, fluorine-containing compound, nitrogen-containing compound, compound containing at least one unsaturated carbon-carbon bond, carboxylic acid anhydride or the mixtures thereof. In some embodiments, the additive is vinyl carbonate, vinyl ethylene carbonate, or a mixture of any two or more such compounds. Further, the additive is present in a range of from 0.01% to 10% by weight.

In some embodiments the additive is a fully or partially halogenated phosphoric acid ester compound, an ionic liquid, or mixtures thereof. The halogenated phosphoric acid ester may include 4-fluorophenyldiphenylphosphate, 3,5-difluorophenyldiphenylphosphate, 4-chlorophenyldiphenylphosphate, trifluorophenylphosphate, heptafluorobutyldiphenylphosphate, trifluoroethyldiphenylphosphate, bis(trifluoroethyl)phenylphosphate, and phenylbis(trifluoroethyl)phosphate. The ionic liquids may include tris(N-ethyl-N-methylpyrrolidinium)thiophosphate bis(trifluoromethylsulfonyl)imide, tris(N-ethyl-N-methylpyrrolidinium) phosphate bis(trifluoromethylsulfonyl)imide, tris(N-ethyl-N-methylpiperidinium)thiophosphate bis(trifluoromethylsulfonyl)imide, tris(N-ethyl-N-methylpiperidinium)phosphate bis(trifluoromethylsulfonyl)imide, N-methyl-trimethyl silylpyrrolidinium bis(trifluoromethylsulfonyl)imide, N-methyl-trimethylsilylpyrrolidinium hexafluorophosphate. Further, the additive is present in a range of 0.01% to 10% by weight.

In one embodiment, the electrochemical energy storage device is a lithium secondary battery. In some embodiments, the secondary battery is a lithium battery, a lithium-ion battery, a lithium-sulfur battery, a lithium-air battery, a sodium ion battery, or a magnesium battery. In some embodiments, the electrochemical energy storage device is an electrochemical cell, such as a capacitor. In some embodiments, the capacitor is an asymmetric capacitor or supercapacitor. In some embodiments, the electrochemical cell is a primary cell. In some embodiments, the primary cell is a lithium/$MnO_2$ battery or Li/poly(carbon monofluoride) battery.

In an embodiment, a secondary battery is provided including a positive and a negative electrode separated from each other using a porous separator and the electrolyte described herein.

Suitable cathode materials for a secondary battery including the electrolyte described herein include those such as, but not limited to, vanadium oxide, lithium peroxide, sulfur, polysulfide, a lithium carbon monofluoride (also known as $LiCF_x$) or mixtures of any two or more thereof, carbon-coated olivine cathodes such as $LiFePO_4$, lithium metal oxides such $LiCoO_2$, $LiNiO_2$, $LiNi_xCo_yMet_zO_2$, $LiMn_{0.5}Ni_{0.5}O_2$, $LiMn_{0.1}Co_{0.1}Ni_{0.8}O_2$, $LiMn_{0.2}Co_{0.2}Ni_{0.6}O_2$, $LiMn_{0.3}Co_{0.2}Ni_{0.5}O_2$, $LiMn_{0.33}Co_{0.33}Ni_{0.33}O_2$, $LiMn_2O_4$, $LiFeO_2$, $Li_{1+x'}Ni_{\alpha}Mn_{\beta}Co_{\gamma}Met'_{\delta}O_{2-z'}F_{z'}$, or $A_{n'}B_2(XO_4)_3$, wherein Met is Al, Mg, Ti, B, Ga, Si, Mn or Co; Met' is Mg, Zn, Al, Ga, B, Zr or Ti; A is Li, Ag, Cu, Na, Mn, Fe, Co, Ni, Cu or Zn; B is Ti, V, Cr, Fe or Zr; X is P, S, Si, W or Mo; and wherein 0≤x≤0.3, 0≤y≤0.5, 0≤z≤0.5, 0≤x'≤0.4, 0≤α≤1, 0≤β≤1, 0≤γ≤1, 0≤δ≤0.4, and 0≤n'≤3. In other embodiments, an olivine cathode has a formula of $Li_{1+x}Fe_{1z}Met''_y$ $PO_{4-m}X'_n$, wherein Met" is Al, Mg, Ti, B, Ga, Si, Ni, Mn or Co; X' is S or F; and wherein 0≤x≤0.3, 0 0≤y≤0.5, 0≤z≤0.5, 0≤m≤0.5 and 0≤n≤0.5.

Suitable anodes include those such as lithium metal, graphitic materials, amorphous carbon, carbon nanotubes, $Li_4Ti_5O_{12}$, tin alloys, silicon, silicon alloys, intermetallic compounds, or mixtures of any two or more such materials. Suitable graphitic materials include natural graphite, artificial graphite, graphitized meso-carbon microbeads (MCMB) and graphite fibers, as well as any amorphous carbon materials. In some embodiments, the anode and cathode electrodes are separated from each other by a porous separator.

In some embodiments, the anode is a composite anode including active materials such as silicon and silicon alloys, and a conductive polymer coating around the active material. The active material may be in the form of silicon particles having a particle size of between about 1 nm and about 100 μm. Other suitable active materials include but are not limited to hard-carbon, graphite, tin, and germanium particles. The polymer coating material can be cyclized using heat treatment at temperatures of from 200° C. to 400° C. to thereby convert the polymer to a ladder compound by crosslinking polymer chains. Specific polymers that can be used include but are not limited to polyacrylonitrile (PAN) where the cyclization changes the nitrile bond (CN) to a double bond (C═N). The polymer material forms elastic but robust films to allow for controlled fragmentation/pulverization of silicon particles within the polymer matrix. Additionally, the PAN matrix also provides a path for Li-ion mobility thus enhancing the conductivity of the composite anode. The resultant anode material can overcome expansion and conductivity challenges of silicon-based anodes, such as by providing binders that can prevent expansion of silicon particles and conductive additives to provide a path for Li-ion mobility. In some embodiments, the polymer is about 10 wt. % to 40 wt. % of the anode composite material. Additional description of these Si-PAN composite anodes is provided in U.S. Pat. Nos. 10,573,884 and 10,707,481, both of which are hereby incorporated by reference in their entirety.

The separator for the lithium battery often is a microporous polymer film. Examples of polymers for forming films include polypropylene, polyethylene, nylon, cellulose, nitrocellulose, polysulfone, polyacrylonitrile, polyvinylidene fluoride, polybutene, or copolymers or blends of any two or more such polymers. In some instances, the separator is an electron beam-treated micro-porous polyolefin separator. The electron treatment can increase the deformation temperature of the separator and can accordingly enhance thermal stability at high temperatures. Additionally, or alternatively, the separator can be a shut-down separator. The shut-down separator can have a trigger temperature above about 130° C. to permit the electrochemical cells to operate at temperatures up to about 130° C.

The disclosure will be further illustrated with reference to the following specific examples. It is understood that these examples are given by way of illustration and are not meant to limit the disclosure or the claims to follow.

Example A—Synthesis of triethyleneglycol-thiolane

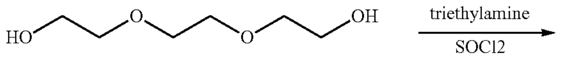

-continued

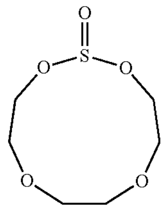

1. To a 100 mL 3-neck flask equipped with a magnetic stirring bar, water-cooled condenser, N2 inlet and thermocouple was added triethyleneglycol and dichloromethane (DCM) (20 mL). Triethylamine was added by pipet and an exotherm to 24° C. was observed. The mixture was cooled to 0° C. in an ice bath.
2. While stirring at 0° C., thionylchloride was slowly added dropwise by syringe. A maximum exotherm to 15° C. was observed and a white solid ppt (triethylamine-HCl) quickly formed. When addition was complete, the ice bath was removed. The colorless mixture slowly returned to RT and stirred for 1 h.
3. DI water (2×20 mL) was added and the mixture was poured into a separatory funnel. The organic phase was extracted into DCM, separated, dried over $MgSO_4$, filtered and the solvent stripped by rotary evaporation to oil. The oil was pumped under high vacuum. The oil was passed through a 0.45 mm GMF filter and dried by vacuum oven (5 mbar, 60° C.). Yield: dense colorless oil, 2.5 g (99%).

FTIR: 2870, 1198, 873, 698 $cm^{-1}$

Example B—Synthesis of Triethyleneglycol phenyl phosphate

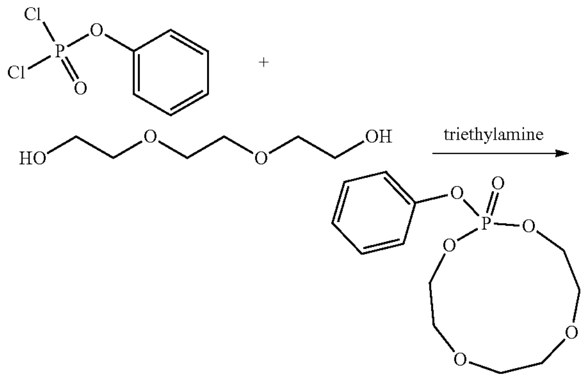

1. To a 40 mL vial equipped with a magnetic stirring bar and thermocouple was added triethylene glycol and DCM (10 mL). Triethylamine was added by pipet and no exotherm was observed.
2. While stirring at RT, phenyldichlorophosphate was slowly added dropwise by syringe. An exotherm to 42° C. was observed and a white solid ppt (triethylamine-HCl) quickly formed. The pale, yellow mixture slowly returned to RT and stirred for 1 h.
3. DI water (2×10 mL) was added and the mixture was poured into a separatory funnel. The organic phase was extracted into DCM, separated, washed with 5% HCl (5 mL), separated, dried over $MgSO_4$ and the solvent stripped by rotary evaporation to oil. Crude yield: dense yellow oil, 1.6 g (>99%).

FTIR: 3459, 2970, 1735, 1364, 1219, 931, 525 cm'.

Example C—Electrolytes for NMC622/Gr Cells

Electrolyte formulations were prepared in a dry argon filled glovebox by combining all the electrolyte components in a glass vial and stirring for 24 hours to ensure complete dissolution of the salts. A functionalized crown ether is added to a base electrolyte formulation including a 3:7 by weight mixture of ethylene carbonate, "EC" and ethyl methyl carbonate, "EMC, and 1 M lithium hexafluorophosphate, "$LiPF_6$", as a $Li^+$ ion conducting salt, dissolved therein. Conventional additives like vinylene carbonate, "VC" and fluoroethylene carbonate, "FEC". Comparative Example 1 (CE1) as shown in Table A. Embodiment Example 1 (EE1) uses a representative example molecule as per the present disclosure. The electrolyte components and additives used in are summarized in Table A.

TABLE A

Electrolyte Formulations for NMC622/Gr cells

| Electrolyte | Base Formulation | Additive Weight (%) |
|---|---|---|
| Comparative Example 1 (CE1) | 1.0M $LiPF_6$ in EC:EMC (3:7) | FEC: 1% VC: 1%, |
| Embodiment Example 1 (EE1) | 1.0M $LiPF_6$ in EC:EMC (3:7) | FEC: 1% Example A: 1% |

Example D—NMC622/Gr Cell Electrochemical Data

The electrolyte formulations prepared are used as electrolytes in 200 mAh Li-ion pouch cells including lithium nickel manganese cobalt oxide (NMC622) cathode active material and graphite as the anode active material. In each cell, 0.9 mL of electrolyte formulation was added and allowed to soak in the cell for 1 hour. The cells are vacuum sealed, and primary charged before wetting at 25° C. for 10 hours. The cells were then charged to 3.8 V at C/25 rate before degassing, followed by vacuum sealing. After degassing, the cells were charged and discharged twice between 4.45 to 3.0 V at C/10 rate, and the results are summarized in Table B. The dQ/dV profiles are shown in FIG. 1, which demonstrates that the addition of the functionalized crown ether results in a reduction peak at 2.4V during the initial charge of the cell. This additional reduction peak indicates a change in the resulting SEI. The AC-IR is the measured internal resistance at 1 kHz, and the reported discharge capacity is for the last first discharge at C/10 rate. Cells with EE1 electrolyte have lower AC-IR values compared to CE1 which is a result of the additive in the electrolyte.

TABLE B

Initial Cell Data for NMC622/Gr cells

| Electrolyte | $1^{st}$ Coulombic Efficiency (%) | Formation Discharge Capacity (mAh) | AC-IR (mΩ) |
|---|---|---|---|
| CE1 | 87.4 | 203.5 | 97.5 |
| EE1 | 86.9 | 200.4 | 92.4 |

Figure 2:
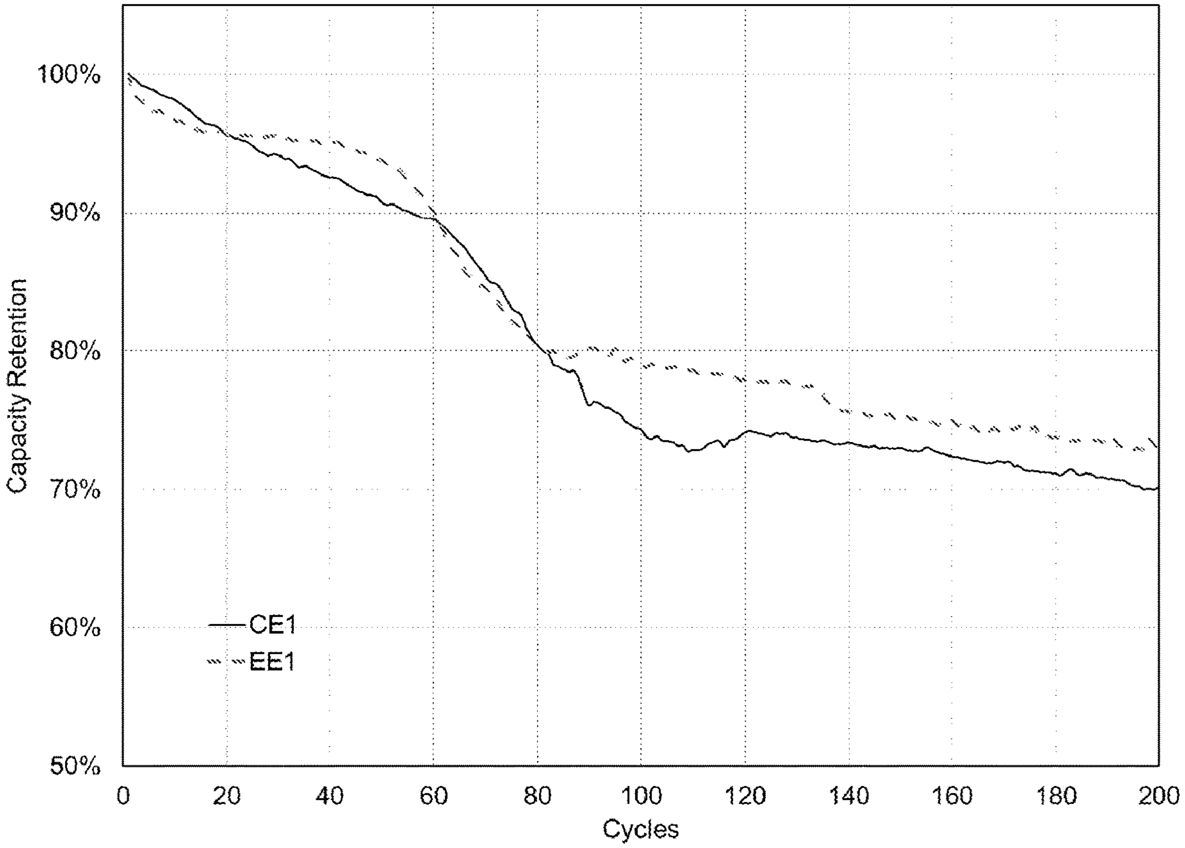
FIG. 2 shows the room temperature cycle life characteristics in a cycle life plot of electrolytes tested in NMC622/Gr cells.

The cells are then charged and discharged two hundred times between 4.45 to 3.0 V at 0.5 C rate at 25° C. As seen in FIG. 2, the discharge capacity retention of cells with EE1 electrolyte are comparable with cells with the CE1, signifying the functionalized crown ether additive can perform a similar function to blends of conventional commercial additives. The capacity retention values are summarized in Table C.

TABLE C

Capacity Retention data for NMC622/Gr cells

| Electrolyte | Capacity Retention after 50 Cycles (%) | Capacity Retention after 100 Cycles (%) |
|---|---|---|
| CE1 | 90.6 | 74.3 |
| EE1 | 93.7 | 79.0 |

Example E—Electrolytes for NMC811/SiO+Gr Cells formulations were prepared in a dry argon filled glovebox by combining all the electrolyte components in a glass vial and stirring for 24 hours to ensure a completely homogeneous mixture. The individual components of the electrolyte formulations are EC, EMC, FEC, 1,3-propanesultone (PaS), ethylene sulfate (ESA), $LiPF_6$, lithium difluorophosphate (LFO), lithium bis(oxalato)borate (LiBOB) and 1,3,6,9-tetraoxa-2-thiacycloundecane-2,2-dioxide (EFCE). The base formulation for all formulations tested was 1M $LiPF_6$ in EC/EMC 30/70 weight basis solvent, with 1.0 wt. % LFO, 1 wt. % LiBOB, 5 wt. % FEC, 0.5 wt. %, PaS, 0.5 wt. % ESA. The embodiment examples use the representative example molecule EFCE as per the present disclosure at a concentration of 1.0 weight percent and is readily miscible in the solution. The electrolyte components and additives used in are summarized in Table D.

TABLE D

Electrolyte Formulations for NMC811/SiO + Gr cells

| Electrolyte | Additive Weight (%) |
|---|---|
| Comparative Example 2 (CE2) | n/a |
| Embodiment Example 2 (EE2) | Embodiment Functional Crown Ether (EFCE): 1,3,6,9-tetraoxa-2-thiacycloundecane-2,2-dioxide 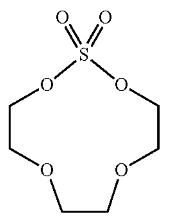 [SMILES: O=S1(=O)OCCOCCOCCO1] 1 wt. % |

Example F—NMC811/SiO+Gr Cell Electrochemical Data

Figure 3:
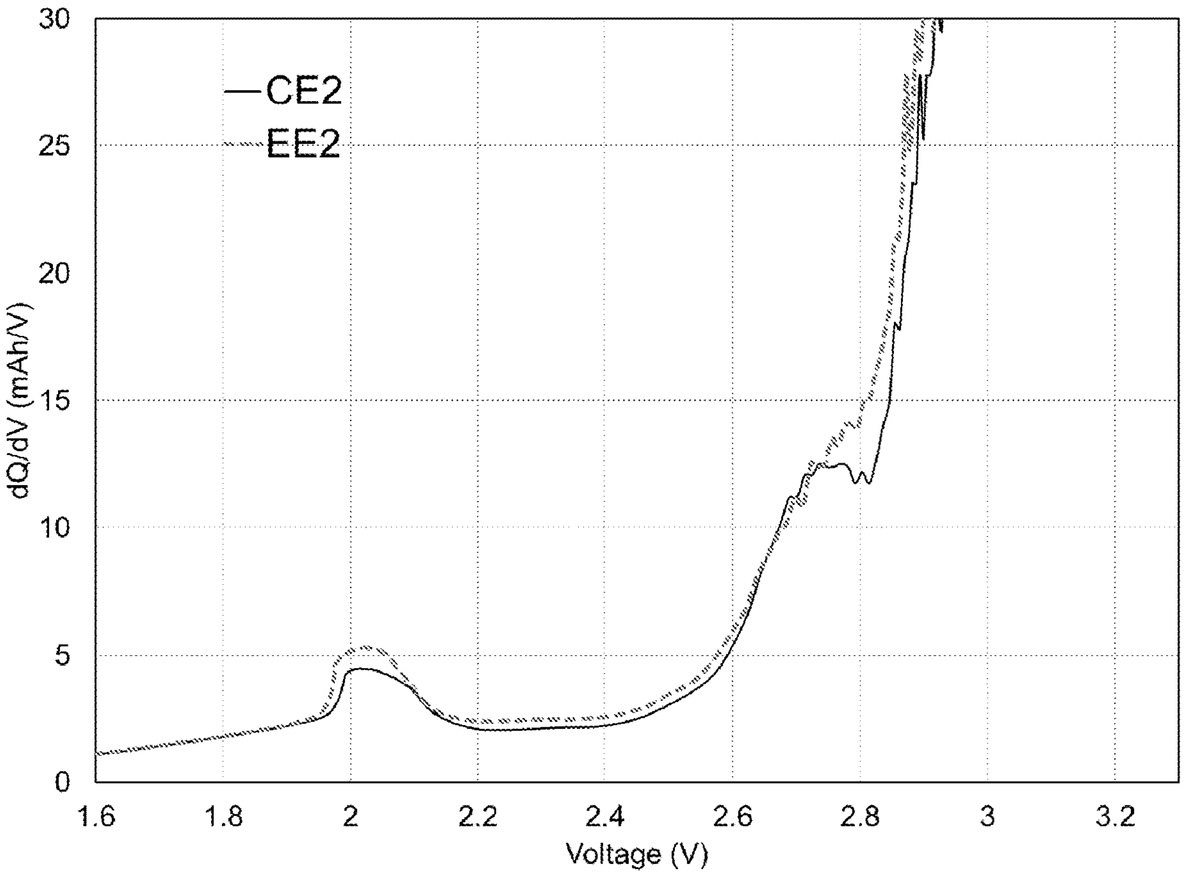
FIG. 3 shows a differential capacity profile of cell formation for the dQ/dV profiles of electrolytes tested in NMC811/SiO+Gr cells.

The electrolyte formulations prepared are used as electrolytes in 900 mAh Li-ion pouch cells including lithium nickel manganese cobalt oxide (NMC811) cathode active material, and graphite combined with silicon oxide in a ratio of 9 to 1 as the anode active material. In each cell, 2.5 mL of electrolyte formulation was added and allowed to soak in the cell for 1 hour. The cells are vacuum sealed, and primary charged before wetting at 25° C. for 24 hours. The cells were then charged to 4.2 V at C/10 rate, discharged to 2.7 V at C/10 rate before degassing, followed by vacuum sealing. After degassing, the cells were charged and discharged twice between 4.2 to 2.7 V at C/10 rate, and the results are summarized in Table E. The dQ/dV profiles are shown in FIG. 3, which demonstrates that the addition of the functionalized crown ether results in a reduction shoulder at 2.8 V during the initial charge of the cell. This additional reduction peak indicates a change in the resulting SEI. The AC-IR is the measured internal resistance at 1 kHz, and the reported discharge capacity is for the last first discharge at C/10 rate. The direct current internal resistance (DCIR) is then collected by applying a 10 second 1 C discharge pulse to the cell and measuring the voltage drop of the cell. Cells with EE2 electrolyte have lower AC-IR and DCIR values compared to CE2 which is a result of the functionalized crown in the electrolyte.

TABLE E

Initial Cell Data for NMC811/SiO + Gr cells

| Electrolyte | Initial Discharge Capacity (mAh) | DCIR (mΩ) | AC-IR (mΩ) |
|---|---|---|---|
| CE2 | 956.0 | 92.9 | 26.6 |
| EE2 | 956.8 | 80.3 | 22.5 |

Figure 4:
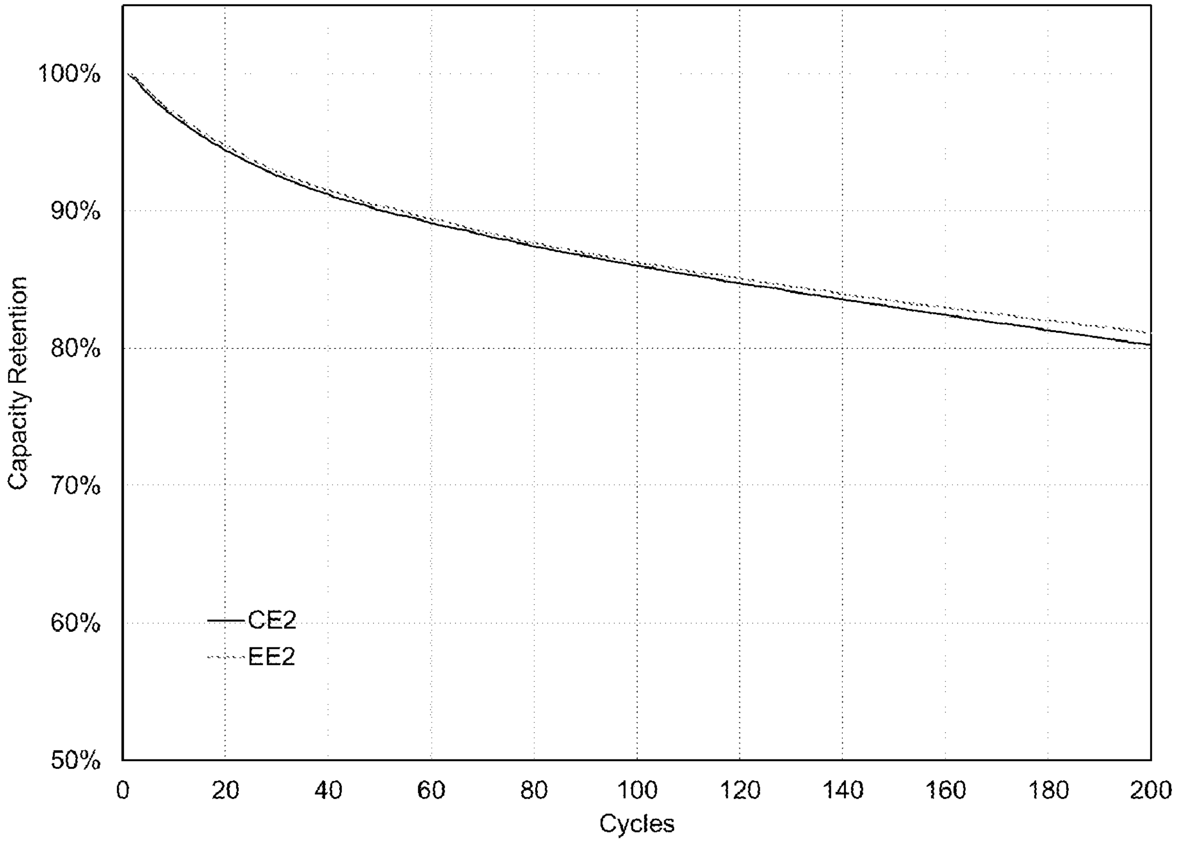
FIG. 4 shows the room temperature cycle life characteristics in a cycle life plot of electrolytes tested in NMC811/SiO+Gr cells.

The cells are then charged and discharged two hundred times between 4.2 to 2.7 V at 1.0 C rate at 25° C. As seen in FIG. 4, the discharge capacity retention of cells with EE2 electrolyte are comparable with cells with the CE2, signifying the functionalized crown ether additive can perform a similar function to blends of conventional commercial additives. The capacity retention values are summarized in Table F.

TABLE F

Capacity Retention data for NMC811/SiO + Gr cells

| Electrolyte | Capacity Retention after 50 Cycles (%) | Capacity Retention after 200 Cycles (%) |
|---|---|---|
| CE2 | 90.0 | 80.0 |
| EE2 | 90.4 | 81.1 |

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. An electrochemical energy storage device electrolyte comprising:

an aprotic organic solvent;

a metal salt; and at least one compound according to formula I, II or III (I)

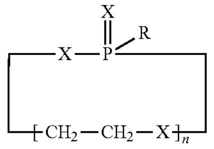

(I)

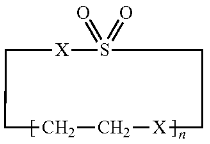

(II)

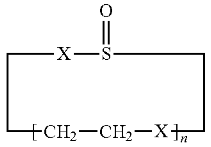

(III)

wherein:

n is an integer ranging from 2 to 8;

X is independently oxygen or sulfur; and

R is independently a halogen, oxygen, or sulfur atom further bonded to a C1-C12 substituted or unsubstituted alkyl groups, a C6-C14 aryl group, a C1-C12 substituted or unsubstituted alkyl group, or a C6-C14 aryl group, wherein any hydrogen atom can be replaced with an epoxide, halogen, alkyl, alkoxy, perfluorinated alkyl, silyl, siloxy, silane, sulfoxide, amide, azo, ether, and thioether group, or a combination thereof or any carbon atom can be unsubstituted or can be substituted with an epoxide, halogen, alkyl, alkoxy, perfluorinated alkyl, silyl, siloxy, silane, sulfoxide, amide, azo, ether, and thioether group, or a combination thereof.

2. The electrolyte of claim 1, wherein the at least one compound according to formula I, II or III is one of the following structures:

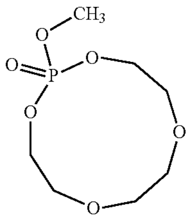

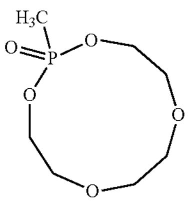

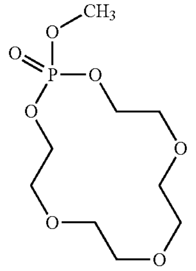

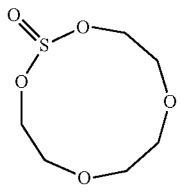

-continued

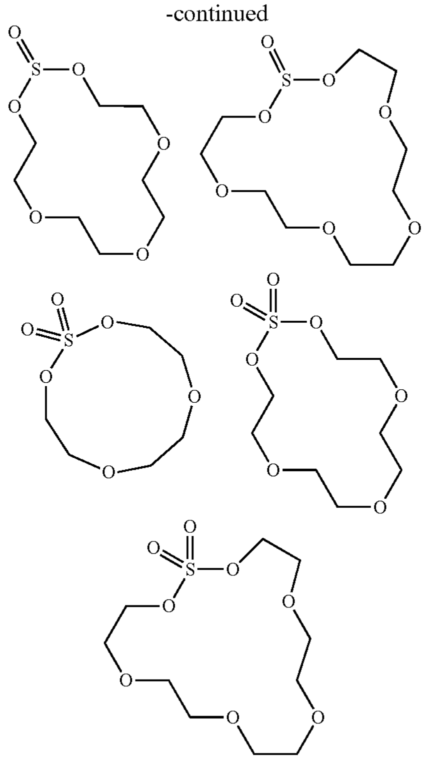

3. The electrolyte of claim 1, wherein the at least one compound according to formula I, II or III is present in a concentration from 0.01 wt. % to 10 wt. % of the electrolyte.

4. The electrolyte of claim 1, wherein the aprotic organic solvent comprises an open-chain or cyclic carbonate, carboxylic acid ester, nitrite, ether, sulfone, ketone, lactone, dioxolane, glyme, crown ether, siloxane, phosphoric acid ester, phosphite, mono-or polyphosphazene or mixture thereof.

5. The electrolyte of claim 1, wherein the aprotic organic solvent is present in a concentration from 50 wt. % to 90 wt. % of the electrolyte.

6. The electrolyte of claim 1, wherein the cation of the metal salt is an alkali metal.

7. The electrolyte of claim 6, wherein the alkali metal is lithium or sodium.

8. The electrolyte of claim 1, wherein the metal salt is present in a concentration from 10 wt. % to 30 wt. % in the electrolyte.

9. The electrolyte of claim 1, further comprising at least one additive.

10. The electrolyte of claim 9, wherein the at least one additive comprises a sulfur-containing compound, a phosphorus-containing compound, a boron-containing compound, a silicon-containing compound, a fluorine-containing compound, a nitrogen-containing compound, a compound containing at least one unsaturated carbon-carbon bond, a carboxylic acid anhydride, an epoxide, or a mixture thereof.

11. The electrolyte of claim 10, wherein the at least one additive is present in a concentration of from 0.01 wt. % to 10 wt. % in the electrolyte.

12. An electrochemical energy storage device comprising:
a cathode;
an anode;
the electrolyte according to claim 1; and
a separator.

13. The device of claim 12, wherein the cathode comprises a lithium metal oxide, spinel, olivine, carbon-coated olivine, vanadium oxide, lithium peroxide, sulfur, lithium polysulfide, a lithium carbon monofluoride or mixture thereof.

14. The device of claim 13, wherein the lithium metal oxide is $LiCoO_2$, $LiNiO_2$, $LiNi_xCo_yMet_zO_2$, $LiMn_{0.5}Ni_{0.5}O_2$, $LiMn_{0.1}Co_{0.1}Ni_{0.8}O_2$, $LiMn_{0.2}Co_{0.2}Ni_{0.6}O_2$, $LiMn_{0.3}Co_{0.2}Ni_{0.5}O_2$, $LiMn_{0.33}Co_{0.33}Ni_{0.33}O_2$, $LiMn_2O_4$, $LiFeO_2$, $Li_{1+x'}Ni_{\alpha}Mn_{\beta}Co_{\gamma}Met'_{\delta}O_{2-z'}F_{z'}$, or $A_{n'}B_2(XO_4)_3$, wherein Met is Al, Mg, Ti, B, Ga, Si, Mn or Co; Met' is Mg, Zn, Al, Ga, B, Zr or Ti; A is Li, Ag, Cu, Na, Mn, Fe, Co, Ni, Cu or Zn; B is Ti, V, Cr, Fe or Zr; X is P, S, Si, W or Mo; and wherein $0 \leq x \leq 0.3$, $0 \leq y \leq 0.5$, $0 \leq z \leq 0.5$, $0 \leq x' \leq 0.4$, $0 \leq \alpha \leq 1$, $0 \leq \beta \leq 1$, $0 \leq \gamma \leq 1$, $0 \leq \delta \leq 0.4$, $0 \leq z' \leq 0.4$ and $0 \leq h' \leq 3$.

15. The device of claim 12, wherein the anode comprises lithium metal, graphitic material, amorphous carbon, Li4TisO2, tin alloy, silicon, silicon alloy, an intermetallic compound, or a mixture thereof.

16. The device of claim 15, wherein the anode is a composite anode comprising an active material comprising silicon or silicon alloy and a conductive polymer coating around the active material.

17. The device of claim 16, wherein the conductive polymer is polyacrylonitrile (PAN).

18. The device of claim 12, wherein the separator comprises a porous separator separating the anode and cathode from each other.

19. The device of claim 18, wherein the porous separator comprises an electron beam-treated micro-porous polyolefin separator or a microporous polymer film comprising nylon, cellulose, nitrocellulose, polysulfone, polyacrylonitrile, polyvinylidene fluoride, polypropylene, polyethylene, polybutene, or a co-polymer or blend of any two or more thereof.

20. The device of claim 12, wherein the aprotic organic solvent comprises an open-chain or cyclic carbonate, carboxylic acid ester, nitrite, ether, sulfone, ketone, lactone, dioxolane, glyme, crown ether, siloxane, phosphoric acid ester, phosphite, mono-or polyphosphazene or mixture thereof.

21. The device of claim 12, wherein the aprotic organic solvent is present in a concentration from 50 wt. % to 90 wt. % in the electrolyte.

22. The device of claim 12, wherein the cation of the metal salt is an alkali metal.

23. The device of claim 22, wherein the alkali metal is lithium or sodium.

24. The device of claim 12, wherein the metal salt is present in a concentration from 10 wt. % to 30 wt. % in the electrolyte.

25. The device of claim 12, wherein the electrolyte further comprises at least one additive.

26. The electrolyte of claim 25, wherein the at least one additive comprises a sulfur-containing compound, a phosphorus-containing compound, a boron-containing compound, a silicon-containing compound, a fluorine-containing compound, a nitrogen-containing compound, a compound containing at least one unsaturated carbon-carbon bond, a carboxylic acid anhydride, an epoxide, or a mixture thereof.

27. The device of claim 25, wherein the at least one additive is present in a concentration ef from 0.01 wt. % to 10 wt. % in the electrolyte.

* * * * *